United States Patent
Raghuraman et al.

(10) Patent No.: US 7,402,424 B2
(45) Date of Patent: Jul. 22, 2008

(54) SPECTROSCOPIC PH MEASUREMENT AT HIGH-TEMPERATURE AND/OR HIGH-PRESSURE

(75) Inventors: Bhavani Raghuraman, Wilton, CT (US); Moin Muhammad, Edmonton (CA); Jinglin Gao, Edmonton (CA); Craig Borman, Camrose (CA); Gale Gustavson, Brookfield, CT (US); Philip Rabbito, Milford, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 11/345,460

(22) Filed: Feb. 1, 2006

(65) Prior Publication Data

US 2007/0178595 A1  Aug. 2, 2007

(51) Int. Cl.
*C12M 1/34* (2006.01)
(52) U.S. Cl. .................................. 435/287.1
(58) Field of Classification Search ........................ None
See application file for complete search history.

(56) References Cited

U.S. PATENT DOCUMENTS

| 2004/0129874 A1 | 7/2004 | Torgersen et al. |
| 2004/0219064 A1 | 11/2004 | Raghuraman et al. |
| 2005/0265649 A1 | 12/2005 | DaSilva et al. |

FOREIGN PATENT DOCUMENTS

| GB | 2395555 A1 | 5/2004 |
| GB | 2412171 A | 9/2005 |
| GB | 2420849 A | 6/2006 |

OTHER PUBLICATIONS

Raghuraman et al. Meeting abstract. ANYL 142 The 23rd ACS national meeting, in Washington, DC, Aug. 28-Sep. 1, 2005.*
Le Peintre, M. M., pH Measurement under pressure and high temperature, Sep. 1960, pp. 584-591, Translation of Abstract Only.
Langmuir, D., Aqueous Environmental Geochemistry, 1997, pp. 20-28, 124-142, Prentice Hall, Upper Saddle River, NJ, USA.
Boreng, R., et al., Downhole Measurement of pH in Oil & Gas Applications by Use of a Wireline Tool, SPE European Formation Damage Conference, 2003, pp. 1-12, SPE 82199, Society of Petroleum Engineers, USA.
Galster, H., pH Measurement Fundamentals, Methods, Applications, Instrumentation, 1991, p. 60, VCH Publishers, Inc., Germany/USA.
Yao, W., et al., Spectrophotometric Determination of Freshwater pH Using Bromocresol Purple and Phenol Red, Environmental Science & Technology, 2001, vol. 35, No. 6, pp. 1197-1201, American Chemical Society, USA.
Martz, T., et al., A Submersible Autonomous Sensor for Spectrophotometric pH Measurements of Natural Waters, Analytical Chemistry, 2003, vol. 75, No. 8, pp. 1844-1850, American Chemical Society, USA.
Buck, R. P., et al., Measurement of pH. Definition, Standards, and Procedures, Pure and Applied Chemistry, 2002, vol. 74, No. 11, pp. 2169-2200, International Union of Pure and Applied Chemistry, USA.
Raghuraman, B. et al., Real-Time Downhole pH Measurement Using Optical Spectroscopy, SPE International Symposium on Oilfield Chemistry, 2005. pp. 1-11, SPE 93057, Society of Petroleum Engineers, USA.
Bates, R., determination of pH Theory and Practice, 1964, pp. 131-171, John Wiley & Sons, Inc. New York, NY, USA.

* cited by examiner

*Primary Examiner*—Jon P Weber
*Assistant Examiner*—Bin Shen
(74) *Attorney, Agent, or Firm*—James McAleenan; Vincent Loccisano; Jody Lynn DeStefanis

(57) ABSTRACT

Methods and apparatuses for high-temperature and high-pressure measurement of pH and/or alkalinity of a fluid is described.

7 Claims, 10 Drawing Sheets

SPECTROSCOPIC PH MEASUREMENT AT HIGH-TEMPERATURE AND/OR HIGH-PRESSURE

TECHNICAL FIELD

The disclosed method and apparatus relate to pH measurement of fluids using pH sensitive reagents and, more particularly, to a method and apparatus that allows accurate pH measurement at high-temperature and/or high-pressure.

BACKGROUND

Accurate measurement of pH is important in diverse fields such as process control, reaction kinetics, environmental and biomedical research and oilfield applications. Many chemical processes require pH monitoring and control at extreme conditions of temperature, pressure, and salinity. However, as will be described below, standard potentiometric techniques provide accurate measurements at moderate temperatures, pressures, and salinities. Measurements of pH of standard buffers at high-temperature and high-pressure using hydrogen and/or glass electrodes have been reported by LePeintre, *Bull. Soc. Franc. Electr.* 1960, 8, 584, and Kryukov, et al. as cited in *pH Measurement: Fundamentals, Methods, Applications, Instrumentation* VCH Publishers, 1991; however, liquid junction instability results in uncertainties in the measurement. Furthermore, pressure balancing needs and liquid junctions make it practically inconvenient to use hydrogen and/or glass electrodes for routine measurements in high-pressure, high-temperature systems. Boreng, et al. in *SPE European Formation Damage Conference*, May 13-14, 2003, The Hague, The Netherlands SPE 82199 describe a solid-state electrode for high-temperature and high-pressure pH measurement. While this proposed method eliminates the liquid junction uncertainty, the pH is measured relative to sodium activity that must be independently determined to determine the absolute pH.

Spectroscopic measurement of pH with very high accuracy using pH-sensitive dyes has been a well-established laboratory technique at ambient conditions since the early 1900's (Bates, *Determination of pH: Theory and Practice*, Chapter 6, John Wiley, 1964). More recently, this technique has been shown to improve precision for seawater and freshwater pH measurements over a range of ionic strengths where potentiometric techniques can prove to be problematic (Yao, et al., *Environ. Sci. Technol.*, 2001, 35, 1197-1201; Martz, et al. *Anal. Chem.*, 2003, 75, 1844-1850). These references cite the advantages of the spectroscopic technique with respect to low drift, reproducibility, and rapidness of the measurement as compared to the standard glass electrodes. Furthermore, because pH measurement depends only on the molecular properties of the indicator dyes, once the dye equilibrium dissociation constants have been characterized, the need for calibration prior to every measurement is eliminated. The methods described above allow implementation of the spectroscopic technique at close to ambient conditions and narrow ionic strength intervals corresponding to either seawater or fresh water conditions, however, the methods do not allow for implementation of the spectroscopic technique at high-temperatures and/or high-pressures.

Because of the lack of robust high-temperature high-pressure pH measurement techniques, currently high-temperature and high-pressure aqueous system equilibrium and the role of pH is characterized using chemical modeling of complex chemical equilibria to calculate the pH. In oilfields, it is important to know the pH of formation fluid to predict corrosion rates, scale formation, water compatibility, etc. Current practice involves collecting fluid samples in single-phase bottles, bringing them to surface and flashing them. The pH at high-temperature high-pressure downhole conditions is obtained by simulations that use ambient flashed gas and water phase analysis as inputs to chemical equilibrium models. This introduces errors in pH measurement due to sample handling, precipitation of ionic solids from flashed water samples and modeling uncertainties of complex ionic equilibria.

Spectroscopic measurement of pH relies on pH-sensitive dyes that can exist in an acid or base form. The optical absorbance spectra of pH-sensitive dyes change as they convert from their acid (A) to base form (B):

$$A \Leftrightarrow B + H^+ \qquad \text{Eq. 1}$$

The fraction of the dye present in the acid and base forms depends on the pH of the solution. The pH is calculated using the following equation:

$$\text{pH} = pK_a + \log\frac{\gamma_B}{\gamma_A} + \log\frac{[B]}{[A]}, \qquad \text{Eq. 2}$$

where $pK_a$ is $-\log_{10} K_a$;

$K_a$ is the thermodynamic equilibrium constant for the dye and is a function of temperature and pressure;

[A] and [B] is the concentration of the acid, base form, respectively, of the dye in the sample; and $\gamma_A$ and $\gamma_B$ is the activity coefficient of the acid, base form of the dye, respectively, and a function of temperature, pressure, and ionic strength of solution. Equation 2 is more commonly written as:

$$\text{pH} = pK'_a + \log\frac{[B]}{[A]}, \qquad \text{Eq. 3}$$

where:

$$pK'_a = -\log_{10}\left(K_a \frac{\gamma_A}{\gamma_B}\right). \qquad \text{Eq. 4}$$

Because pKa' includes the activity coefficients, it is no longer only a function of pressure and temperature, but also a function of ionic strength. Calibration at ambient conditions using standard buffers of known pH is well established. A two-wavelength measurement allows calculation of [B]/[A] and hence the determination of the pH of unknown solutions using Equation 3.

The challenge is in extending this technique to higher temperatures and pressures where there are no standard calibrating buffers. The International Union of Pure and Applied Chemistry (IUPAC) 2002 guidelines for pH measurement using standard electrodes are valid only to 50° C., 1 bar, and ionic strengths below 0.1 gmol/kg (see Buck et al., *Measurement of pH Definition, Standards and Procedures—IUPAC Recommendations* 2002, *Pure and Applied Chemistry*, 2002, Vol. 74, Issue 11. At higher temperatures, pressures, and ionic strengths, there are inherent uncertainties associated with liquid junction potentials; because of this uncertainty, currently there are no guidelines for making pH measurements under these conditions. Standard buffer solutions are typically certified at room temperatures. When buffer solutions are heated or their salinity (ionic strength) is changed, their pH values change and as a result they are no longer the original pH certified standards.

Raghuraman et al. in *Real-Time Downhole pH Measurement Using Optical Spectroscopy*, SPE International Symposium on Oilfield Chemistry, Feb. 2-4, 2005, Houston, Tex., USA, SPE 93057 describe a methodology for calibration and extension of the spectroscopic measurement to higher temperatures and pressures. Standard buffer solutions are simple salts whose chemical equilibria have been reported over a range of temperature, pressure, and salinity conditions. As a first step to calibrating dyes for pH measurements at high-temperature and high-pressure conditions, one could use models of standard salt buffer equilibria to calculate pH at these conditions. Using these pH values for calibration, one can determine pKa' of various pH-sensitive dyes as a function of temperature (to 150° C.), pressure (to 680 bar) and ionic strength (to 3 mol/kg). The dyes chosen should be ones that can survive and have pH sensitivity under these conditions. Once pKa' is known, Eq. 3 can be used to calculate pH at any temperature, pressure, and ionic strength by measuring the dye-sample spectra.

Commonly owned Great Britain Patent No. 2,395,555, entitled "Apparatus and Method for Analyzing Downhole Water Chemistry," incorporated by reference herein in its entirety, teaches a method of using dyes to measure pH in high temperature pressure oil wells at downhole conditions.

Commonly owned United States Patent Application Publication Number 20040128974, filed Sep. 22, 2003, entitled "Determining fluid chemistry of formation fluid by downhole reagent injection spectral analysis," incorporated herein by reference in its entirety, teaches a method for analyzing formation fluid in earth formation surrounding a borehole that includes storing analytical reagent in a container in a fluids analyzer in a formation tester and moving the formation tester, including the reagent, downhole. Reagent from the reagent container is injected into formation fluid in the flowline to make a mixture of formation fluid and reagent. The mixture is moved through a spectral analyzer cell in the fluids analyzer to produce a time-series of optical density measurements at a plurality of wavelengths. A characteristic of formation fluid is determined by spectral analysis of the time-series of optical density measurements.

Single dyes are typically sensitive to only about 1.5 units on either side of their pKa. To make measurements over a wide range of pH, one has to either use many single dyes or alternatively use a dye mixture. Commonly owned United States Patent Application Publication Number 20040219064, filed Feb. 19, 2004, entitled "Spectroscopic pH measurement using optimized reagents to extend measurement range," incorporated herein by reference in its entirety, teaches an indicator mixture that allows pH measurement over a broader range of pH or to a higher accuracy than available using conventional spectroscopic techniques. In particular, the mixture of the present invention is comprised of two or more reagents such that when combined, the reagent mixture is capable of either detecting: (1) a pH range broader or more accurate than the reagent individually, or (2) pH more accurately than the reagents individually. Also disclosed are methods of making and using the mixture. This methodology allows high-accuracy, extended-range pH measurement with a single dye mixture (see FIGS. 1 and 2). Raghuraman et al. in *Real-Time Downhole pH Measurement Using Optical Spectroscopy*, SPE International Symposium on Oilfield Chemistry, Feb. 2-4, 2005, Houston, Tex., USA, SPE 93057 report pH measurements in high-temperature, pressure oil wells using these techniques and apparatuses.

As mentioned earlier, today there is standard IUPAC recommendation or any spectroscopic method for high-temperature, high-pressure and high-ionic strength measurement of pH in the laboratory. Conventional potentiometric techniques work only to temperatures of 50° C., 1 bar and ionic strength below 0.1 gmol/kg. Thus, there is a need for high-temperature and high-pressure measurements of pH in the laboratory.

SUMMARY

In a first embodiment, the present invention relates to an apparatus for high-temperature and high-pressure measurement of pH of a fluid, the apparatus comprising: a fluid sample chamber to receive a fluid sample at a measurement pressure in operable communication with a first pressure regulating means, wherein the first pressure regulating means is configured to ensure that the pressure does not drop below the measurement pressure; a dye chamber in fluid communication with the fluid sample chamber, and in operable communication with a second pressure regulating means, wherein the second pressure regulating means is configured to ensure that the pressure does not drop below the measurement pressure; a light source and a detector in optical communication with the interior of the fluid sample chamber; and a spectral analyzer, wherein the spectral analyzer is configured to analyze the optical density of a mixture of the fluid sample and dye.

In a second embodiment, a method of high-temperature and high-pressure measurement of pH of a fluid is further disclosed, the method comprising: a. inputting an amount of dye solution into a dye chamber; b. inputting an amount of water into a fluid sample chamber; c. adjusting the pressure of the dye solution and the water to a measurement pressure; d. measuring a spectrum of the water; e. displacing the water with the fluid sample, while ensuring that the pressure does not drop below the measurement pressure; f. measuring a spectrum of the fluid sample; g. inputting a desired amount of the dye solution into the fluid sample chamber; and h. measuring a spectrum of the dye solution and the fluid sample mixture. Further, the pH of the fluid sample may be determined using the measured spectrum.

In a third embodiment, an apparatus for high-temperature and high-pressure measurement of pH of a fluid, the apparatus comprising: a container capable of withstanding high-pressure and high-temperature; a light source and a detector in optical communication with the interior of the high-pressure, high-temperature container; a first pressure regulator having a first volume chamber in fluid communication with the high-pressure, high-temperature container, wherein the first pressure regulator is configured to ensure that the first volume chamber does not drop below a measurement pressure; a second pressure regulator having a second volume chamber in fluid communication with the high-pressure, high-temperature container, wherein the second pressure regulator is configured to ensure that the second volume chamber does not drop below the measurement pressure; a fluid sample container capable of withstanding high-pressure and high-temperature in fluid communication with the first volume chamber; a dye reservoir in fluid communication with the second volume chamber; and a spectral analyzer to receive data gathered by the detector wherein the spectral analyzer is configured to analyze the optical density of a mixture of a fluid sample and a dye to determine the pH of the fluid sample.

In a fourth embodiment, a method of high temperature and high pressure measurement of pH of a fluid is further disclosed, the method comprising: a. filling lines, pump cylinders, and a container capable of withstanding high temperature and high pressure with water at a measurement pressure; b. measuring the spectrum of the water; c. displacing at least a portion of the water with a fluid sample at measurement pressure, while ensuring that the pressure does not drop below the measurement pressure; d. measuring the spectrum of the fluid sample at measurement pressure; e. mixing a known amount of a dye solution with the fluid sample, while ensuring that the pressure does not drop below the measurement pressure; and f. measuring the spectrum of the dye/fluid sample mixture at measurement pressure. Further, the pH of the dye/fluid sample mixture may be determined from the spectrum of the dye/fluid sample mixture.

In a fifth embodiment, a method to obtain total alkalinity of a fluid sample is disclosed, comprising: a. inputting an acid-dye solution into a dye chamber; b. inputting water into a fluid sample chamber, wherein the fluid sample chamber is at a measurement pressure and temperature; c. measuring the spectrum of the water; d. displacing the water with a fluid sample, while maintaining measurement pressure; e. measuring the spectrum of fluid sample; f. inputting an amount of the acid-dye solution into the fluid sample chamber, while maintaining measurement pressure; g. measuring a spectrum of the dye solution and fluid sample mixture; h. determining the pH of the fluid sample; i. repeating (e), (f), (g), and (h) one or more times to develop a relationship between pH and acid-volume; j. determining the alkalinity of the fluid sample from the relationship.

In a sixth embodiment, an apparatus for high temperature, high pressure measurement of pH of a fluid is disclosed, the apparatus comprising: a flowline to receive a fluid sample in fluid communication with a process line, wherein the flowline is configured so that it may be isolated from the process line; a dye injector in fluid communication with the flowline, wherein the flowline, process line and dye injector are maintained at or above a measurement pressure; a light source located downstream of the dye injector and in optical communication with the interior of the flowline; and a spectral analyzer in communication with the detector.

BRIEF DESCRIPTION OF THE DRAWINGS

The present disclosure will be better understood by those skilled in the pertinent art by referencing the accompanying drawings, where like elements are numbered alike in the several figures, in which.

DETAILED DESCRIPTION

Throughout the present disclosure the terms reagent and dye are used interchangeably.

Figure 1:
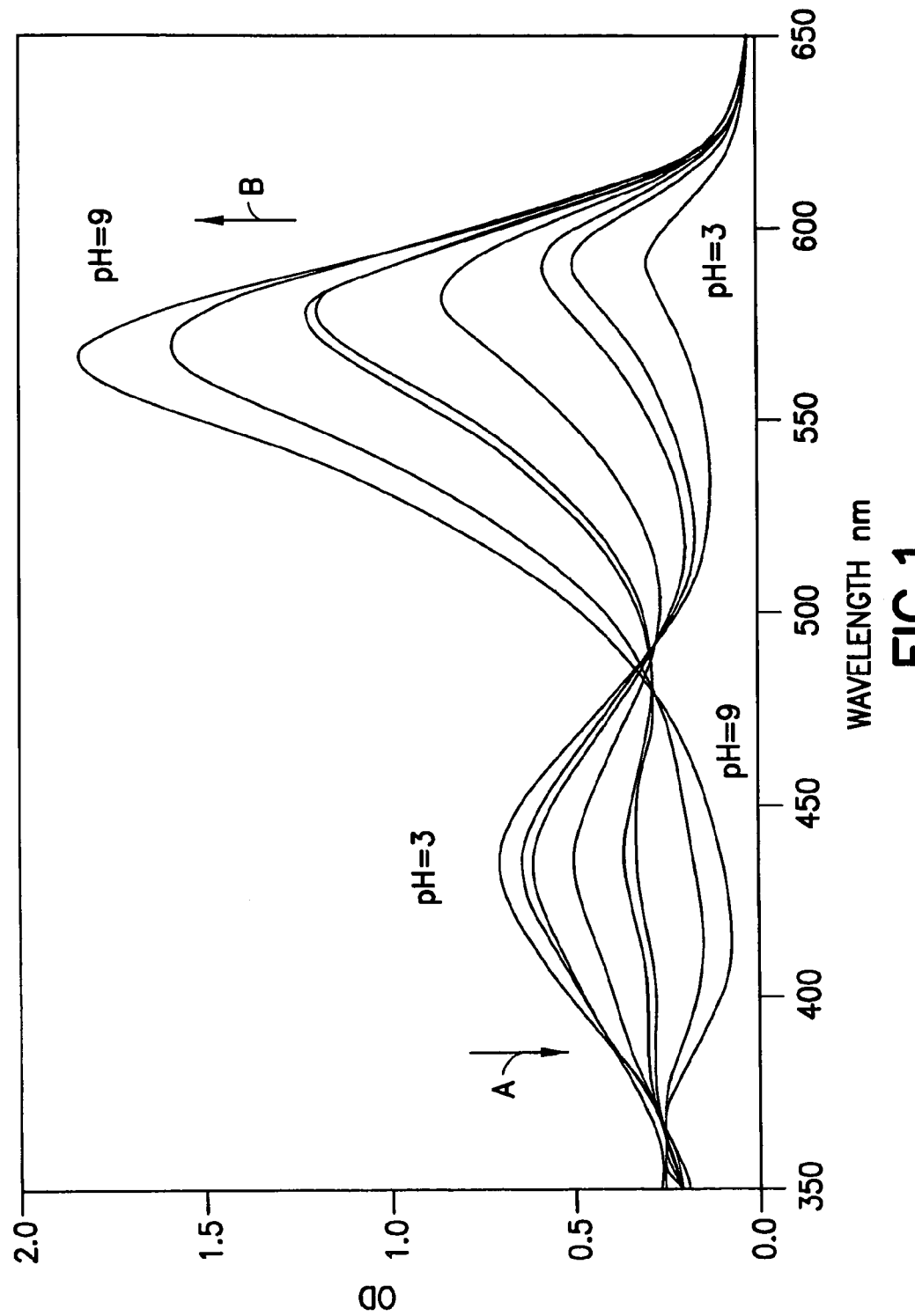
FIG. 1 is a plot showing the spectra (optical density (OD) versus wavelength) of a three-reagent mixture in buffer solution with pH varying from 3 to 9.

FIG. 1 shows experimentally measured spectra for a three-reagent mix in pH buffers 3-9. Arrow A indicates decrease in OD of acid forms of reagents as buffer pH increases from 3 to 9. Arrow B indicates increase in OD of base forms of the reagents as buffer pH increases from 3 to 9.

Figure 2A:
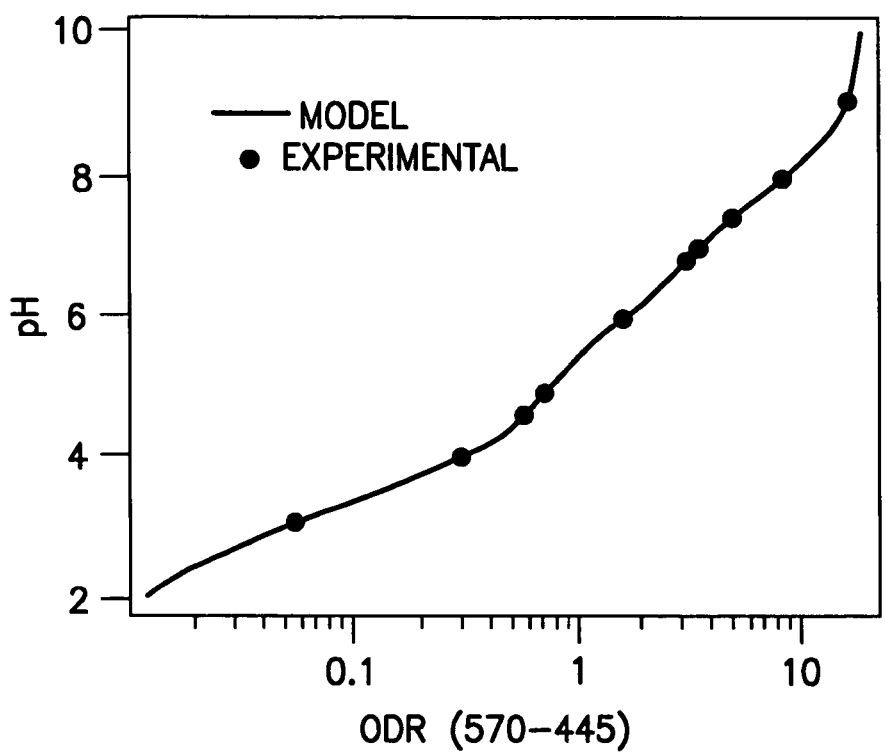
FIGS. 2(a) and (b) are plots: (a) comparing model predicted pH from experimental optical density ratios (ODR) values of FIG. 1 with true buffer pH values (445 and 570 nm wavelengths) and (b) showing the error in pH measurements as a function of pH.
Figure 2B:
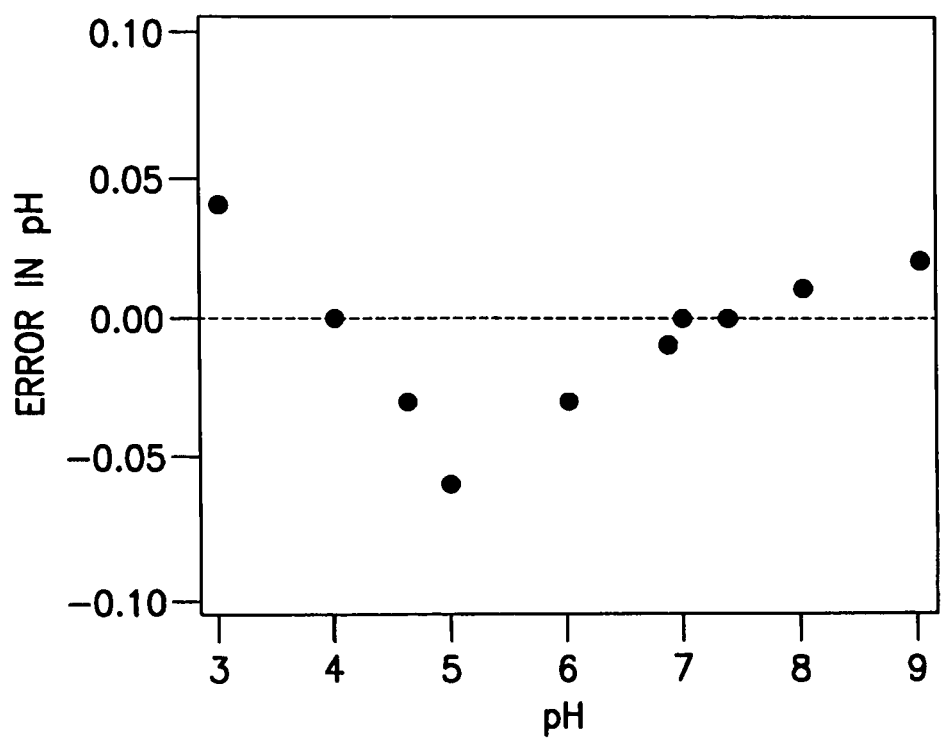

FIG. 2(a) compares model-predicted pH values calculated using measured ODR values of FIG. 1 with true pH values of the buffer solutions. Properties of the reagents used in the mixture are summarized in Table 1. FIG. 2(b) is a plot of the experimental error at various pH values. The reagent mixture of the example of FIG. 2(b) is accurate over the range of buffers used (pH 3-9) with the errors within 0.06 pH units. Accordingly, the reagent mixture used in the apparatus and methodology of the present invention is accurate over a broader pH range than the traditional single reagent indicators, which typically work over 2-3 pH units (see, for example, Table 2 below).

TABLE 1

Summary of reagent properties used in the model of FIG. 2a.

| | Phenol Red (reagent 1) | | Chlorophenol Red (reagent 2) | | Bromophenol Blue (reagent 3) | |
|---|---|---|---|---|---|---|
| | Acid | Base* | Acid | Base* | Acid | Base* |
| $\epsilon$ at 570 nm ($\lambda_2$) | 108 | 37975 | 58 | 54247 | 378 | 46859 |
| $\epsilon$ at 445 nm ($\lambda_1$) | 17916 | 3352 | 18136 | 1985 | 21711 | 1981 |

TABLE 1-continued

Summary of reagent properties used in the model of FIG. 2a.

|  | Phenol Red (reagent 1) | | Chlorophenol Red (reagent 2) | | Bromophenol Blue (reagent 3) | |
| --- | --- | --- | --- | --- | --- | --- |
|  | Acid | Base* | Acid | Base* | Acid | Base* |
| Mol. wt. | 354.38 | 376.36 | 423.28 | 445.26 | 669.98 | 691.97 |
| pKa | 7.79 | | 6.11 | | 4.11 | |

*The base form is a sodium salt of the reagent.

TABLE 2

Extending range of pH measurements with reagent mixtures for 0.1 pH unit desired accuracy assuming spectroscopic noise of 0.01 OD units

| Reagent | Mole Fraction ($f_1$, $f_2$, $f_3$) | $C_T$, [M] | pH range |
| --- | --- | --- | --- |
| Phenol Red (PR) | 1.0, 0.0, 0.0 | $2 \times 10^{-5}$ | 6.6-8.7 |
| Chlorophenol Red (CPR) | 0.0, 1.0, 0.0 | $2 \times 10^{-5}$ | 4.7-7.0 |
| Bromophenol Blue (BB) | 0.0, 0.0, 1.0 | $2 \times 10^{-5}$ | 2.8-5.1 |
| PR-CPR | 0.55, 0.45, 0.0 (equal weight fractions) | $2 \times 10^{-5}$ | 5.1-8.2 |
| PR-CPR | 0.55, 0.45, 0.0 (equal weight fractions) | $4 \times 10^{-5}$ | 4.8-8.6 |
| PR-CRP-BB | 0.42, 0.35, 0.23 (equal weight fractions) | $2 \times 10^{-5}$ | 3.6-7.9 |
| PR-CRP-BB | 0.46, 0.26, 0.28 (optimized for pH 3.5 to 8) | $2 \times 10^{-5}$ | 3.5-8.1 |
| PR-CRP-BB | 0.42, 0.35, 0.23 (equal weight fractions) | $4 \times 10^{-5}$ | 3.2-8.5 |

Figure 3:
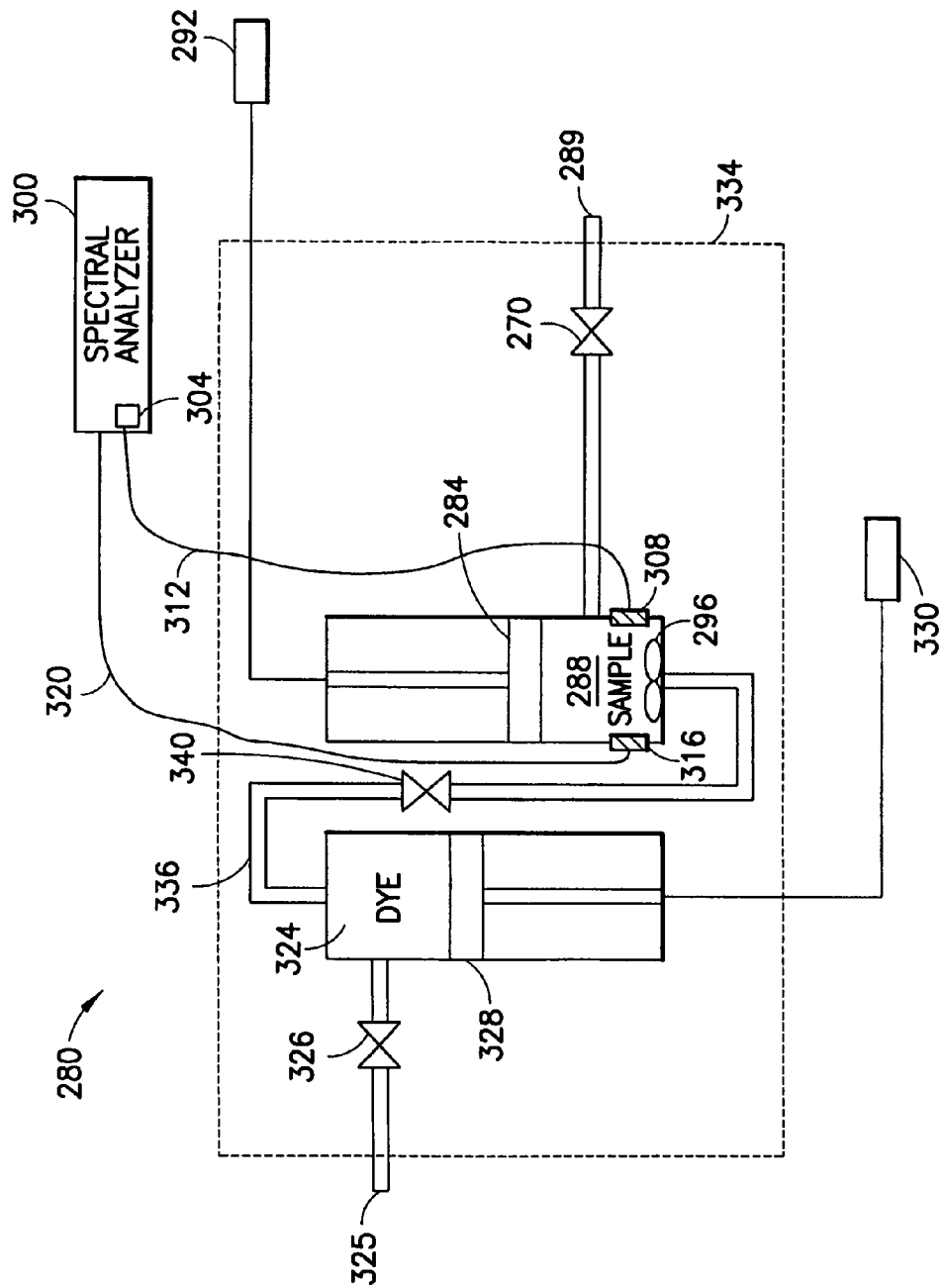
FIG. 3 is a schematic view of a piston/chamber embodiment of the present invention for spectroscopic pH measurement at high-temperature and high-pressure.

FIG. 3 shows an embodiment of the disclosed apparatus 280 for spectroscopic pH measurement at high-temperature and high-pressure in a laboratory environment. A first pressure regulating means 284 and fluid sample chamber 288 are shown. The first pressure regulating means may be a device such as a fluid sample piston. The fluid sample chamber 288 has a fluid sample chamber inlet/outlet 289 which allows fluid sample to be pumped into the chamber 288 or removed from the chamber 288. The fluid sample chamber inlet/outlet 289 has a valve 290 that controls the inflow and outflow of fluid into the chamber 288. The pressure regulating means 284 is in operable communication with an actuator 292. The fluid sample chamber 288 may have a mixer means 296 in fluid communication with it. The mixer means 296 may mix the fluid using mixing or shaking techniques. The fluid sample chamber 288 is in optical communication with a spectral analyzer 300. A light source 304 may be controlled by the spectral analyzer 300. The light source may transmit light through a fiber optic line 312 to a first optical port 308 located on the chamber 288. The fiber optic line provides optical communication between the chamber interior and the light source 304. In alternative embodiments, the light source may be located adjacent to the optical port 308 or may be located within the chamber 288. Spectral information from the fluid sample chamber 288 may be transmitted through a second optical port 316 through a fiber optic line 320 to a detector (not shown). A spectral analyzer 300 analyzes data obtained by the detector. It should be obvious to one of ordinary skill in the art that other configurations for locations and communications between the light source and detector are available with respect to the disclosed apparatus.

The fluid sample chamber 288 is in fluid communication with a dye chamber 324 via a line 336. The line has a valve 340. The dye chamber 324 is in operable communication with a second pressure regulating means 328. The second pressure regulating means may be a dye piston. The dye chamber 324 has a dye chamber inlet/outlet 325 which allows for dye to be placed in or removed from the chamber 324. The dye chamber inlet/outlet 325 has a valve 326 that controls the inflow and outflow of fluid into the chamber 324. The second pressure regulating means 328 is in operable communication with an actuator 330. The chambers 288 and 324 are located in an oven 334, or any other suitable heating device, which can be configured to heat the contents of the chambers 288, 324 and to control the measurement temperature. The pressure and volume within the dye chamber 324 and fluid sample chamber 288 are controlled and adjusted by the pressure regulating means 328, 284, respectively (in this embodiment, the position of the pistons). The fluid flow schemes are controlled by opening and closing the valves 270, 326, 340 and operating the pistons 284, 328. Of course, one of ordinary skill in the art will understand that other types of pumps may be used in this embodiment, including, but not limited to syringe type pumps.

Figure 4A:
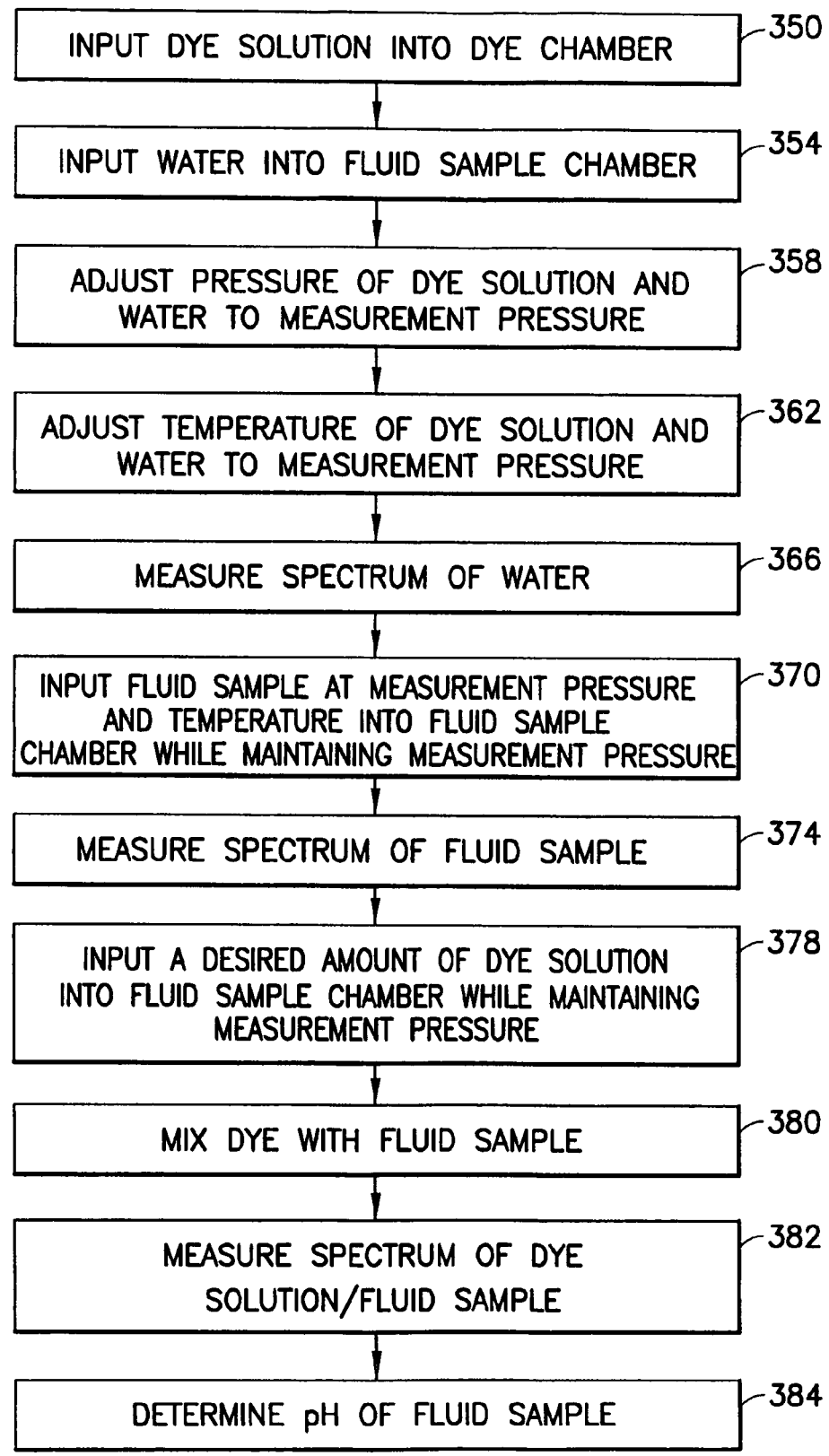
FIGS. 4(a), (b) and (c) are flow charts illustrating an embodiment of a method of the present invention for determining pH measurements: 4(a) shows a flowchart illustrating an embodiment of the disclosed method for spectroscopic pH measurement at high-temperature and high-pressure that may be used with the embodiment shown in FIG. 3; 4(b) shows a flowchart illustrating an embodiment of the disclosed method for determining the pressure sensitivity of pH; and 4(c) shows a flowchart illustrating an embodiment of the disclosed method for determining the temperature sensitivity of pH.

FIG. 4a shows a flowchart illustrating an embodiment of the disclosed method for spectroscopic pH measurement at high-temperature and high-pressure. This method may be used in association with the apparatus shown in FIG. 3. At act 350, a dye solution is inputted into the dye chamber. At act 354, water (preferably deionized water) is inputted into the fluid sample chamber. At act 358, the pressure of the dye solution and water is adjusted to the desired pressure (also referred to as the "measurement pressure"). These pressure adjustments may of course be accomplished with the first pressure regulating means 284 and the second pressure regulating means 328. At act 362 (optional), the temperature of the dye solution and water is adjusted to a desired temperature (also referred to as the "measurement temperature"), such as with the oven 334. At act 366, the spectrum of the water is measured, to obtain a baseline spectrum of the water, and may be used to verify that the spectral analyzer is operating properly. At act 370, a fluid sample at measurement temperature and pressure displaces the water while ensuring that the pressure does not drop below the measurement pressure. It is noted that displacement of the water with the fluid sample is one non-limited method to ensure that the appropriate pressure is maintained. One skilled in the art would appreciate that additional methodologies and apparatuses may be used. The fluid sample is of course the fluid of interest for which pH readings at high-pressure and high-temperature is desired. At act 374 the spectrum of the fluid sample at measurement temperature and pressure is measured. This spectrum may be used as a baseline for comparison with the spectrum of the fluid sample and dye solution mixture. At act 378, a desired amount of dye solution is inputted into the fluid sample chamber, again while ensuring that the measurement pressure is maintained. At act 380, the mixer 296 may be operated to mix the dye solution and fluid sample together. At act 382, a spectrum of the dye solution and fluid sample is measured. Based on the spectra, the pH of the fluid sample can be determined at act 384. If pressure and temperature sensitivity information is desired, the steps in either or both of FIGS. 4b and 4c may be incorporated.

Figure 4B:
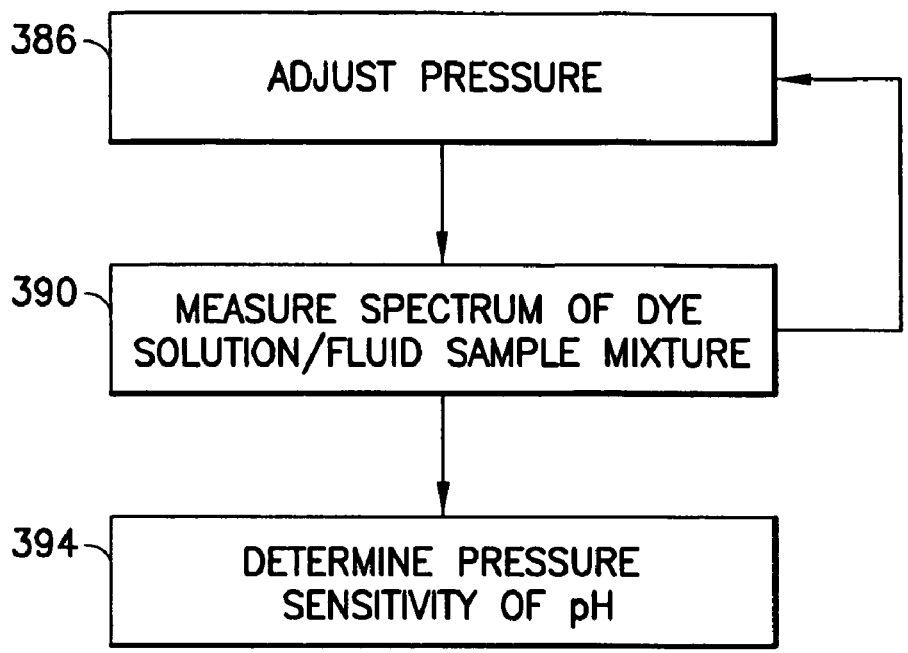
Figure 4C:
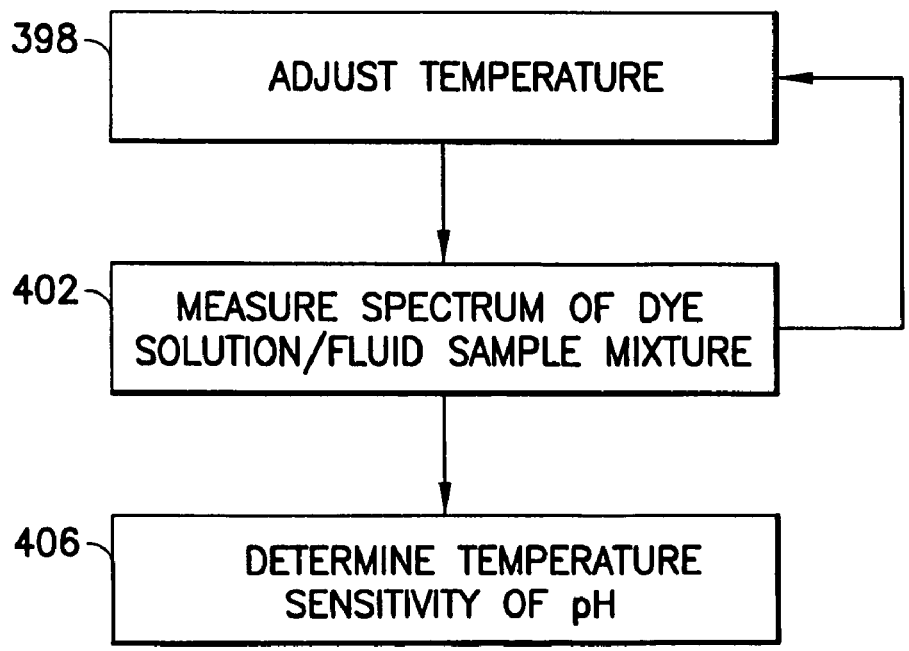

Referring now to FIG. 4b, at act 386, the pressure of the fluid sample and dye is adjusted. At act 390, the spectrum of the dye solution and fluid sample mixture is measured. At this point, acts 386 and 390 may be repeated in order to develop enough data points so that at act 394, the pressure sensitivity of pH for the fluid sample may be determined. Referring now to FIG. 4c, at act 398, the temperature of the dye solution and fluid sample mixture may be adjusted. At act 402, the spectrum of the dye solution and fluid sample mixture may be measured. And, acts 398 and 402 may be repeated in order to develop enough data points so that at act 406, the temperature sensitivity of pH for the fluid sample may be measured. One of ordinary skill in the art will recognize that temperature sensitivity measurements and pressure sensitivity measurements need not be both performed, nor does one need to be performed after or before the other. It should be noted that changing the pressures and temperatures may cause phase transitions in the fluid sample, which may lead to measurable changes in pH that may be of interest in certain applications. Thus, phase sensitive pH measurements may also be obtained and characterized using the methods of the present invention.

One of ordinary skill in the art will recognize that many tests can be developed using the disclosed apparatus to generate the pH profile of a high-temperature and/or high-pressure fluid as a function of temperature, pressure, and amount of solution gas (i.e. when pressure is reduced to below the bubble point pressure and solution gas is discharged from the fluid). Additionally, the high-temperature and/or high-temperature pH profile may be developed for a commingling of two or more liquid streams. Similarly tests may be run to determine the pH profile for various compositions at high-temperature and/or high-pressure.

Standard laboratory methods for the determination of total alkalinity of a fluid typically involves titrating a known volume of the fluid with an acid in the presence of a calorimetric indicator (such as methyl purple) or a potentiometric electrode. Total alkalinity is defined as the point in the titration curve where all carbonate species are neutralized to undissociated carbonic acid or dissolved $CO_2$ (also referred to as the "end point") and is typically found at a pH of about 4.5. With a colorimetric indicator like methyl purple, the end point corresponds to a color change from green to purple, which can be monitored spectroscopically. Alternatively, if pH measurements are also recorded continuously with acid addition, inflections in the titration curves (pH vs. volume of acid added) can also be used to calculate hydroxide alkalinity and carbonate alkalinity in addition to total alkalinity using standard methods reported in literature (see Langmuir, *Aqueous Environmental Geochemistry*, Prentice-Hall, Inc. 1997). This calculation method can then be used to estimate the total carbonate and bicarbonate concentration in the sample as well. Currently, there are no means to measure alkalinity for high-temperature and pressure samples.

The current method and apparatus can be modified to conduct such a titration at high-temperature and high-pressure to measure alkalinity. One could use an acid-dye solution mixture in the dye chamber 324 (see FIG. 3) and charge the fluid sample chamber 288 with a sample fluid. Small fixed volumes of acid-dye solution can be added to the fluid sample chamber 288. Either a calorimetric dye like methyl purple could be used for determining the end point with color change, or an acid-dye mix could be used to record pH simultaneously during the titration to determine the inflection point. When the end point is reached, the total volume of acid added is known because the exact amount of acid-dye solution transmitted from the chamber 324 to the fluid sample chamber 288 is known.

Figure 5:
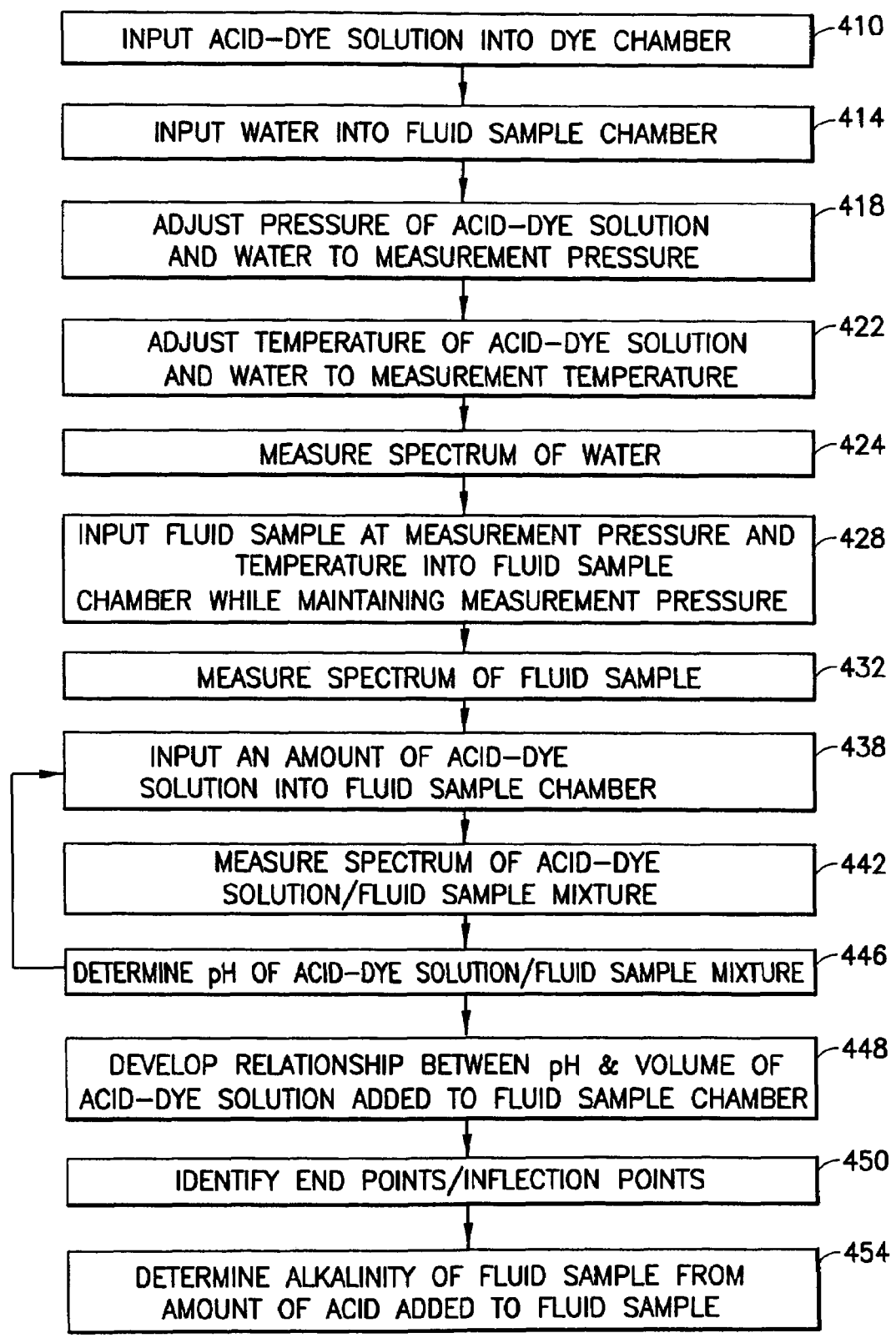
FIG. 5 is a flowchart illustrating an embodiment of a method of the present invention for determining alkalinity of a fluid at high-temperature and high-pressure.

FIG. 5 shows a flowchart illustrating an embodiment of the disclosed method for titration at high-temperature and high-pressure to obtain total alkalinity. This method may be used in association with the apparatus shown in FIG. 3. At act 410, an acid-dye solution is inputted into the dye chamber 324. The dye is preferably a dye mixture that allows extended range pH measurement as described above. At act 414, water (again, preferably deionized water) is inputted into the fluid sample chamber 288. At act 418, the pressure of the acid-dye solution and water is adjusted to the measurement pressure. This pressure adjustment may of course be accomplished with the first pressure regulating means 284 and the second pressure regulating means 328. At act 422, the temperature of the acid-dye solution and water is adjusted to a measurement temperature. This temperature adjustment may be accomplished using oven 334. At act 424, the spectrum of the water is measured to obtain a baseline spectrum of the water, which may be used to verify that the spectral analyzer 300 is operating properly. At act 428, a fluid sample at measurement temperature and pressure displaces the water while ensuring that the pressure does not drop below the measurement pressure. The fluid sample is of course the fluid of interest for which a total alkalinity measurement at high-pressure and high-temperature is desired. At act 432 the spectrum of the fluid sample is measured. This spectrum may be used as a baseline for comparison with the spectrum of the fluid sample and acid-dye solution mixture. At act 438, an amount of acid-dye solution is inputted into the fluid sample chamber 288, again while ensuring that the pressure does not drop below the measurement pressure. During this act, the mixer 296 may be operated to mix the dye solution and fluid sample together. At act 442, a spectrum of the acid-dye and fluid sample mixture (in chamber 288) is measured. Based on the spectra, the pH of the acid-dye fluid sample mixture can be determined at act 446 and the relationship between pH and volume of the acid-dye solution added to the fluid sample chamber is developed at act 448. It is noted that acts 438, 442, and 446 may be repeated to acquire data to develop the relationship of 448. One output of this relationship may be a titration curve. At act 450, the relationship between pH and acid volume is analyzed to determine if the end point has been reached. If the end point has been reached, then the total alkalinity of the original fluid sample can be determined (at act 454) from the amount of acid added to the fluid sample. Further, intermediate inflection points may be used to determine the hydroxide and carbonate alkalinity as described earlier.

Figure 6:
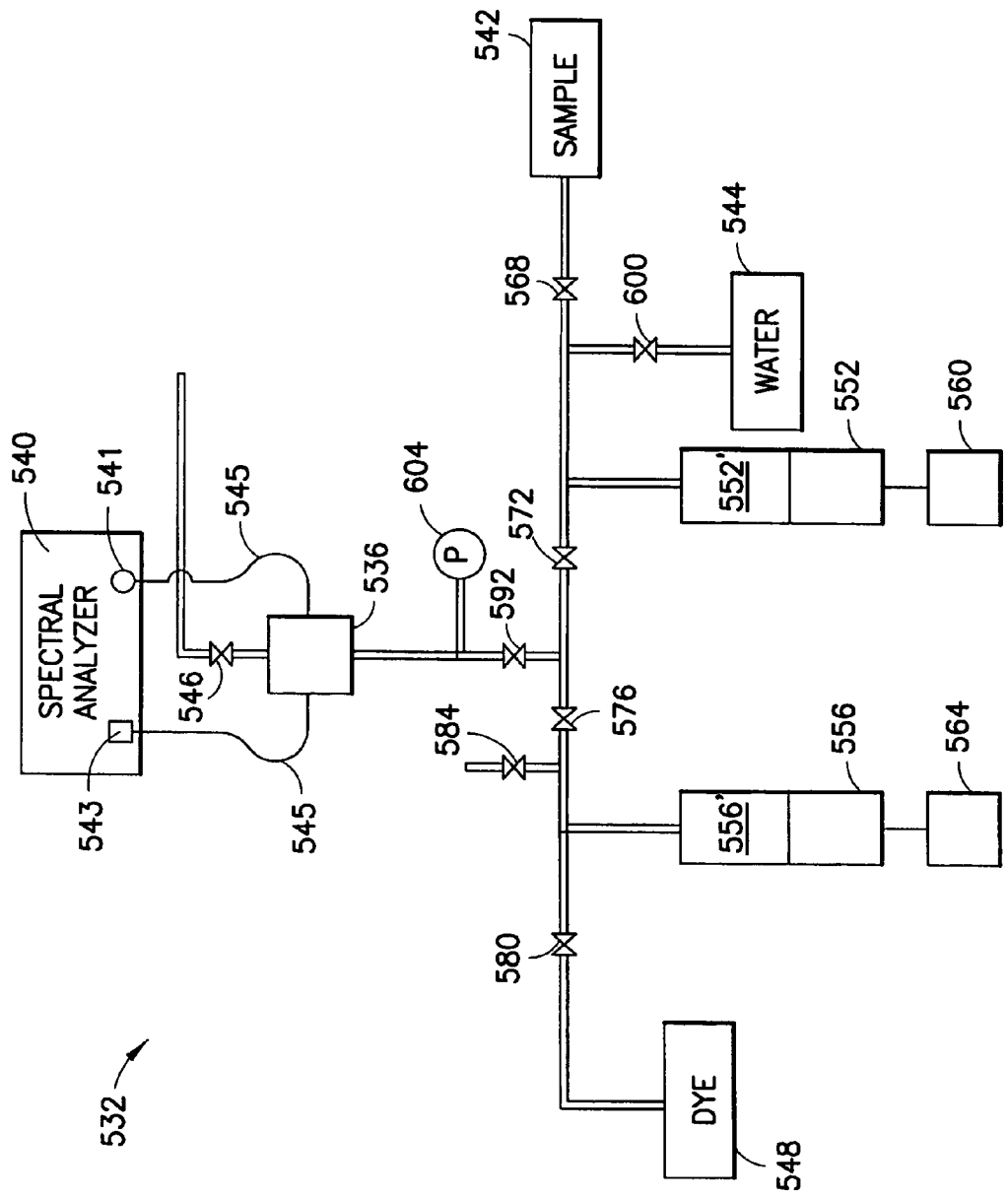
FIG. 6 is a schematic view of a syringe pump embodiment of the present invention for spectroscopic pH measurement at high-temperature and high-pressure.

A second embodiment of the apparatus of the present invention 532 for spectroscopic pH measurement at high-temperature and high-pressure is shown in FIG. 6. In this embodiment the apparatus 532 comprises a high-pressure high-temperature container 536 in optical communication with a spectral analyzer 540. The spectral analyzer 540 may contain a light source 541 and a detector 543. A data transmission means 545, such as, but not limited to fiber optic lines, allow communication between the light source 541 and the interior of the container 536, as well as communication between the detector 543 and the interior of the container 536. It should be obvious to one of ordinary skill in the art that other configurations for location of the light source 541 and detector 543 are available with respect to the disclosed apparatus. The spectral analyzer 540 is configured to spectrally analyze the light transmitted through the container 536. A fluid sample container 542, water reservoir 544, and dye reservoir 548 are all in fluid communication with the container 536. The water held in the water reservoir is preferably deionized water. A first pressure regulator means 552 having a volume chamber 552' to hold a fluid is in fluid communication with and located between the high-temperature and high-pressure container 536 on the one hand, and the fluid sample container 542 and water reservoir 544 on the other. A second pressure regulator means 556 having a volume chamber 556' to hold a fluid is in fluid communication with and located between the dye reservoir 548 and the high-pressure high-temperature container 536. The pressure regulators 552, 556 may be any suitable means, such as pumps, including but not limited to, syringe or piston type pumps. The pressure regulators 552,556 are in communication with actuators 560, 564. Valves 568, 572, 576, 580, 584, 592, 546, 600 are located throughout the system to isolate various components and to allow the delivery of fluids to and from the high-pressure, high-temperature container 536 at different controlled pressures. A pressure transducer 604 is in fluid communication with the high-pressure high-temperature container 536. The actuators 560, 564, valves 546 through 600, pressure transducer 604 and spectral analyzer 540 may be each be in signal communication with a controller (not shown) that is configured to open and close the various valves, and operate the pressure regulators 552, 556 such that fluids at specified pressures, specified temperatures, and specified combinations, mixtures or individual doses of fluid sample, water, and dye may be delivered to the high-pressure high-temperature container 536. In an alternative embodiment, the entire apparatus 532, except for the spectral analyzer 540, pressure regulators 552, 556, and controller may be located in an oven or heat jacket to provide controlled heat to the apparatus 532. In still other embodiments, other controllable heat sources may be used to heat the apparatus 532 such as but not limited to heating elements.

Figure 7A:
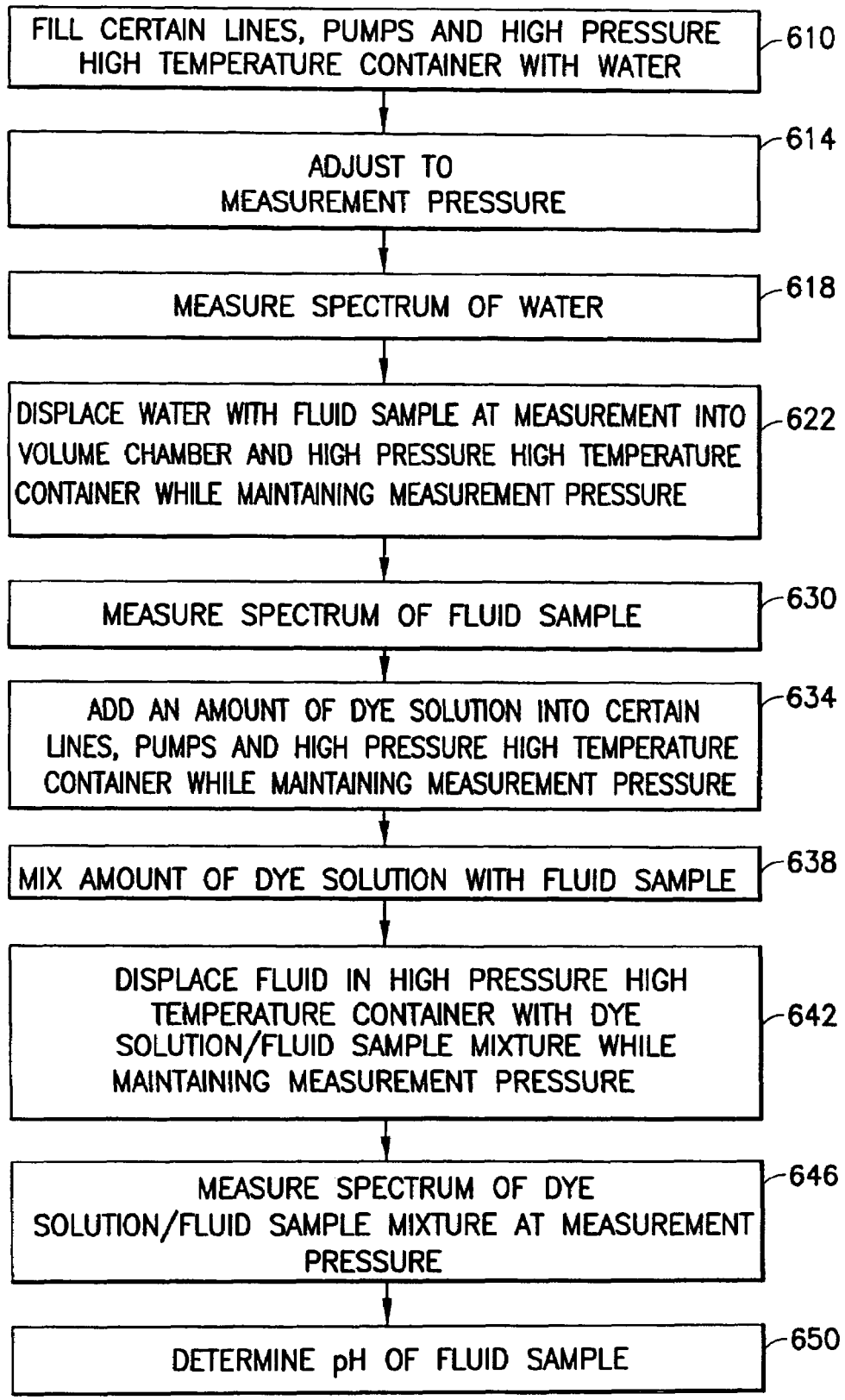
FIGS. 7(a), (b) and (c) are flow charts illustrating an embodiment of a method of the present invention for determining pH measurements: 7(a) shows a flowchart illustrating an embodiment of the disclosed method for spectroscopic pH measurement at high-temperature and high-pressure; 7(b) shows a flowchart illustrating an embodiment of the disclosed method for determining the pressure sensitivity of pH; and 7(c) shows a flowchart illustrating an embodiment of the disclosed method for determining the temperature sensitivity of pH.

FIG. 7a shows a flowchart illustrating one embodiment of the disclosed method for spectroscopic pH measurement at high-temperature and high-pressure. This method may be used in association with the apparatus shown in FIG. 6. At act 610, the lines (except the lines in the dye section to the left of valve 576 in FIG. 6—it is noted that reference to "left" is used for convenience in reference to the configuration shown in FIG. 6), pump chambers 556' and 552', and the high-pressure high-temperature container 536 is filled with water (preferably deionized water). At act 614, the pressure is adjusted to the measurement pressure. At act 618, the spectrum of the water is measured. This may be done in order to obtain a baseline spectrum of water and may be used to verify that the spectral analyzer is operating properly. At act 622, a fluid sample at measurement pressure is inputted into lines and volume chamber 552' and the high pressure high temperature container 536 to displace the water while ensuring that the pressure does not drop below the measurement pressure. As described in previous embodiments, one non-limiting method of ensuring that the measurement pressure is maintained is to displace the water in certainlines, a volume chamber, and the high-pressure, high-temperature chamber 536 with the fluid sample. The fluid sample is that fluid for which pH measurement is ultimately desired. The pressure of the fluid sample is to be maintained at the measurement pressure. At act 630, the spectrum of the fluid sample is measured. This spectrum may be used as a baseline for comparison with the spectrum of the fluid sample and dye mixture. At act 634, an amount of dye is withdrawn from the dye reservoir and used to fill the lines and volume chamber in the section to the left of valve 576 at measurement pressure. (Alternatively, if the system is not at measurement pressure, the system may then be pressurized to the measurement pressure.) At act 638, the pressurized dye is mixed with the fluid sample. The mixing may be accomplished by operating valves as required to pump dye from the pump 556 into the chamber 552', where the dye begins mixing with the sample. Then the dye/sample can be sent from the first volume chamber 552' back to the second volume chamber 556', thereby providing more mixing of the dye and sample. Of course, the sample may first be sent into second volume 556' to mix with the dye, and then the dye/sample can be sent back to the first volume 552'. At act 642, the dye and fluid sample are allowed to mix over a period of time. The period of time will depend on the amount of time necessary for the dye and fluid sample to properly mix and allow for meaningful measurements. The fluid in the lines and the high-pressure high-temperature container is then displaced while maintaining measurement pressure by the dye/sample fluid mixture at act 642. At act 646, the spectrum of the dye and fluid sample mixture is measured at measurement pressure. Based on the spectra, the pH of the fluid sample can be determined at act 650. If more information about the sample fluid is desired, more measurements may be made, which are discussed with respect to FIGS. 7b and 7c.

Figure 7B:
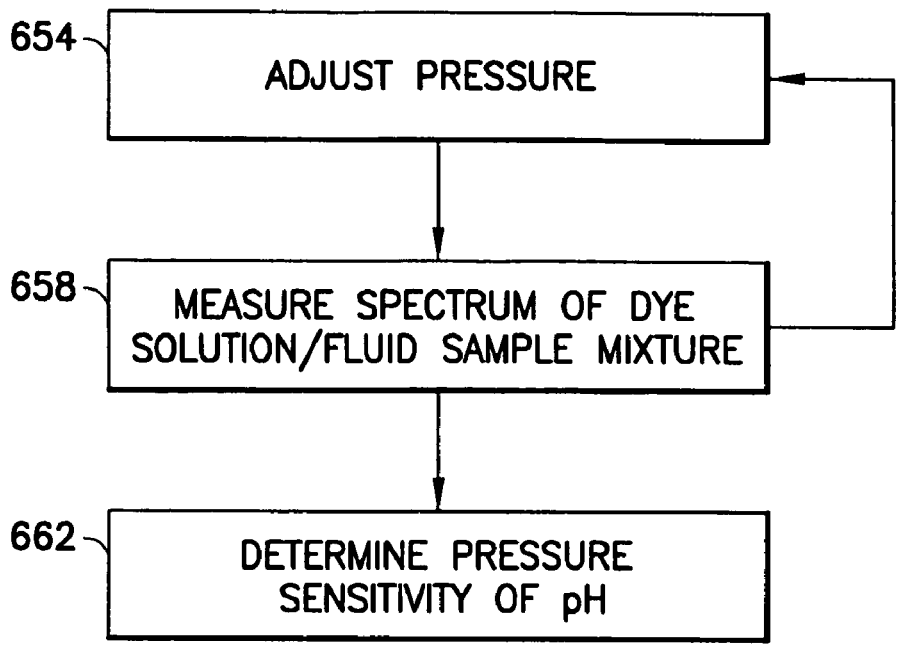
Figure 7C:
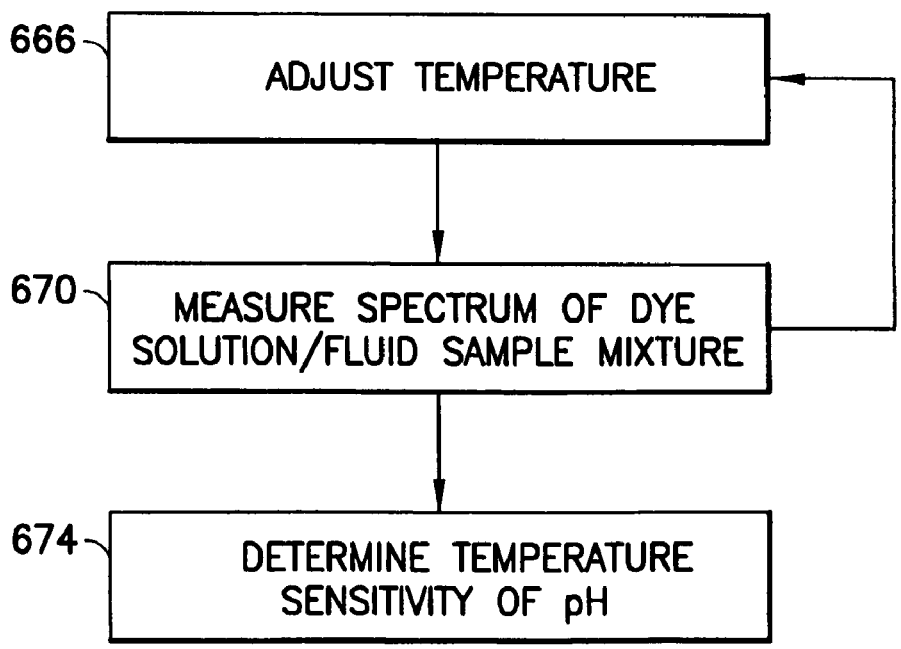

Referring now to FIG. 7b, at act 654, the pressure of the fluid sample and dye is adjusted. At act 658, the spectrum of the dye and fluid sample mixture is measured. At this point, acts 654 and 658 may be repeated in order to develop enough data points so that at act 662, the pressure sensitivity of pH for the fluid sample may be determined. Now referring to FIG. 7c, at act 666, the temperature of the dye and fluid sample mixture may be adjusted. At act 670, the spectrum of the dye and fluid sample mixture may be measured. And, acts 666 and 670 may be repeated in order to develop enough data points so that at act 674, the temperature sensitivity of pH for the fluid sample mixture may be determined. It should be noted that it may be desirable to maintain pressure at some percentage higher than desired measurement pressure (such as 10% higher, for example) while replacing and mixing the fluids to ensure that during displacements and mixing the pressure never accidentally drops below measurement pressure. If the fluids drop below measurement pressure, this may cause any dissolved gas to come out of solution and that can change the sample and its pH.

The system may be adjusted to any desired measurement temperature by using the heating element described in connection with FIG. 6.

Figure 8:
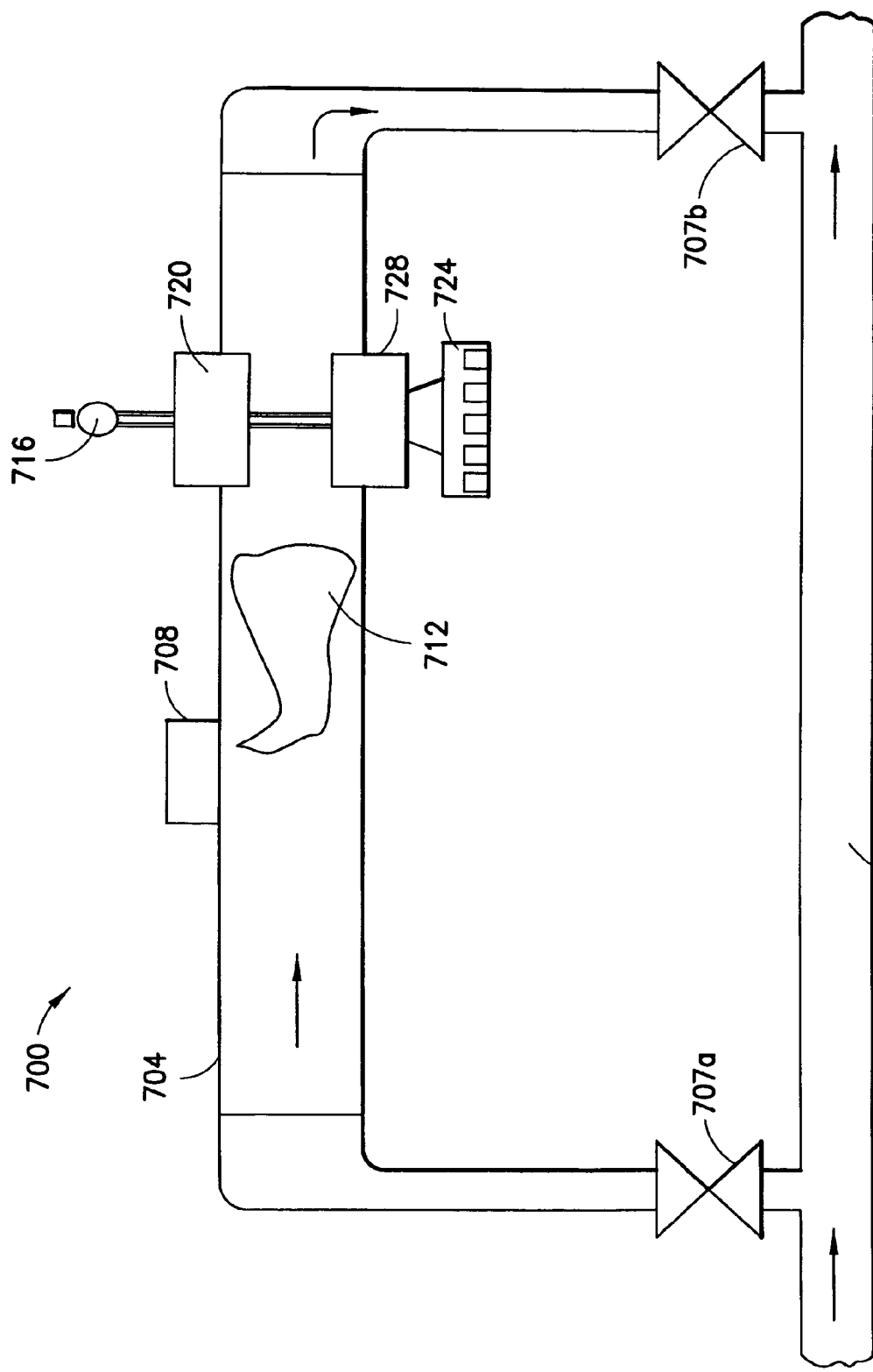
FIG. 8 is a schematic view of an "in flow" embodiment of the disclosed apparatus of the present invention for spectroscopic pH measurement at high-temperature and high-pressure.

FIG. 8 shows an "in-flow" embodiment of an apparatus 700 for spectroscopic pH measurement at high-temperature and high-pressure. The apparatus comprises a flowline 704. The flowline 704 may be in fluid communication with a process line 706, wherein the pH of the fluid in the process is monitored and/or pH determined. Valves 707a and 707b may be located on the flowline 704 to isolate the apparatus 700 from the process line 706. In the embodiment shown in FIG. 8, the flowline 704 is shown connecting back with the process line 706 via the downstream valve 707b. The sample travels in the flowline in the direction of the arrow. A dye injector 708 is located on the flowline 704 and is configured to inject a dye 712 into the flowline 704 to mix with the flowing fluid sample. A light source 716 is located downstream from the dye injector 708. The light source may be external to the flowline 704, but adjacent to an optical port 720, such as a window for instance, located on the flowline. The port 720 is configured to allow light from the light source 716 to enter the flowline 704. A detector 724 is located downstream of the dye injector, and generally opposed to the light source 716. The detector is configured to obtain data from the light emanating from the light source 716 and traveling through the sample and dye 712 mixture. The detector 724 may transmit the data to a spectral analyzer, or the detector 724 may itself have spectral analyzing capacity. The detector 724 may be external to the flowline 704 and adjacent to the optical port 728 as shown in FIG. 8, or alternatively may be located on the flowline 704. The optical port is configured to allow light to exit the flowline 704 and enter the detector 724. All the components in fluid communication with the flowline 704 should be rated for high-temperature and high-pressure. The apparatus 700 may be used for high-temperature and/or high-pressure continuous flow processes and reaction systems where online pH monitoring is needed. The apparatus 700 may use periodic dye injection into the flowline 704 to allow for in situ pH measurements. Such in situ pH measurements may be used with feedback control loops for pH control in processes and reactions where pH is required to be maintained at prescribed levels. In another embodiment, flowline 704 may simply be routed to a disposal means (not shown) via downstream valve 707b, hence allowing a sample to be withdrawn from the process line 706 and then disposed of once the pH measurement is completed, if one wishes to avoid downstream contamination of the process sample with the dye.

The disclosed high-temperature high-pressure pH measuring apparatus and method of the present invention has many advantages. The apparatuses and methods allow for the accurate measuring of pH at extreme conditions. The disclosed apparatus allows for accurate mixing of dye and fluid samples at extreme conditions in order to determine the pH of the fluid sample. Additionally, the disclosed methods and apparatuses allow for the titration of fluids at high-temperature and high-pressure.

It should be noted that the terms "first", "second", and "third", and the like may be used herein to modify elements performing similar and/or analogous functions. These modifiers do not imply a spatial, sequential, or hierarchical order to the modified elements unless specifically stated.

While the disclosure has been described with reference to several embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiments disclosed as the best mode contemplated for carrying out this disclosure, but that the disclosure will include all embodiments falling within the scope of the appended claims.

What is claimed is:

1. A method of high-temperature and high-pressure measurement of pH of a fluid, the method comprising:
   a. inputting an amount of dye solution into a dye chamber;
   b. inputting an amount of water into a fluid sample chamber;
   c. adjusting the pressure of the dye solution with a first pressure regulating means and adjusting the pressure of the water with a second pressure regulating means to a measurement pressure;
   d. measuring a spectrum of the water;
   e. displacing the water with a fluid sample, while ensuring that the second pressure does not drop below the measurement pressure;
   f. measuring a spectrum of the fluid sample;
   g. inputting a desired amount of the dye solution into the fluid sample chamber, while ensuring that the first pressure does not drop below the measurement pressure; and
   h. measuring a spectrum of the dye solution and the fluid sample mixture;
   i. determining the pH of the fluid sample using the measured spectrum.

2. The method of claim 1, further comprising:
   maintaining the temperature of the dye solution and the water to a measurement temperature prior to measuring the spectrum of the water.

3. The method of claim 1, further comprising:
   adjusting the pressure of the dye solution and the fluid sample mixture to one or more additional measurement pressures;
   measuring a spectrum of the dye solution and the fluid sample mixture; and
   determining a pressure sensitivity of the pH of the fluid sample.

4. The method of claim 2, further comprising:
   adjusting the temperature of the dye solution and the fluid sample mixture to one or more additional measurement temperatures;
   measuring a spectrum of the dye solution and the fluid sample mixture; and
   determining a temperature sensitivity of the pH of the fluid sample.

5. A method of high temperature and high pressure measurement pH of a fluid, the method comprising:
   a. filling lines, pump cylinders, and a container capable of withstanding high temperature and high pressure with water at a measurement pressure and a measurement temperature, such that the container is in operable communication with at least one pressure regulating means and at least one temperature regulating means;
   b. measuring the spectrum of the water;
   c. displacing at least a portion of the water with a fluid sample at measurement pressure and temperature, while ensuring that the pressure does not drop below the measurement pressure and the temperature is maintained at the measurement temperature;
   d. measuring the spectrum of the fluid sample at measurement pressure and temperature;
   e. mixing a known amount of a dye solution with the fluid sample, while ensuring that the pressure does not drop below the measurement pressure and the temperature is maintained at the measurement temperature; and
   f. measuring the spectrum of the dye/fluid sample mixture at measurement pressure and temperature;
   g. determining the pH of the dye/fluid sample mixture from the spectrum of the dye/fluid sample mixture.

6. The method of claim 5, further comprising:
   h. adjusting the pressure of the dye/fluid sample mixture to one or more additional measurement pressures;
   i. measuring the spectrum of the pressure adjusted dye/fluid sample mixture;
   j. determining the pressure sensitivity of the pH of the fluid sample using the spectrum of (i).

7. The method of claim 5, further comprising:
   h. adjusting the temperature of the dye/fluid sample mixture to one or more additional measurement temperatures;
   i. measuring the spectrum of the temperature adjusted dye/fluid sample mixture;
   j. determining the temperature sensitivity of the pH of the fluid sample using the spectrum of (i).

\* \* \* \* \*